(12) United States Patent
O'Brien et al.

(10) Patent No.: US 12,131,816 B2
(45) Date of Patent: Oct. 29, 2024

(54) HEALTH TRACKING DEVICE

(71) Applicant: VIAVI Solutions, Inc., San Jose, CA (US)

(72) Inventors: Nada A. O'Brien, Santa Rosa, CA (US); Curtis R. Hruska, Cloverdale, CA (US); Marc K. Von Gunten, Novato, CA (US); Christopher G. Pederson, Santa Rosa, CA (US); Changmeng Hsiung, Redwood City, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 514 days.

(21) Appl. No.: 17/248,488

(22) Filed: Jan. 27, 2021

(65) Prior Publication Data
US 2021/0151165 A1 May 20, 2021

Related U.S. Application Data

(63) Continuation of application No. 16/375,221, filed on Apr. 4, 2019, now Pat. No. 10,950,335, which is a
(Continued)

(51) Int. Cl.
*A61B 5/00* (2006.01)
*A61B 5/0205* (2006.01)
(Continued)

(52) U.S. Cl.
CPC .......... *G16H 20/30* (2018.01); *A61B 5/0075* (2013.01); *A61B 5/0205* (2013.01);
(Continued)

(58) Field of Classification Search
CPC ..... A61B 5/0205; A61B 5/113; A61B 5/1102; A61B 5/0255; A61B 2560/0257;
(Continued)

(56) References Cited

U.S. PATENT DOCUMENTS 9,212,996 B2 12/2015 Watson et al.
10,251,597 B2 4/2019 O'Brien et al.
(Continued)

FOREIGN PATENT DOCUMENTS

CN 103970998 A 8/2014
CN 104303185 A 1/2015
(Continued)

OTHER PUBLICATIONS

DBLP, "An Adaptive Network-Based Fuzzy Inference System (ANFIS) for the Prediction of Stock Market Return: The Case of the Istanbul Stock Exchange," Jan. 2010, 6 pages.
(Continued)

*Primary Examiner* — Rex R Holmes
(74) *Attorney, Agent, or Firm* — Harrity & Harrity, LLP

(57) ABSTRACT

A device may receive, from a plurality of sensors, sensor data relating to a user. The device may include a plurality of types of sensors including a spectrometer and one or more of an accelerometer, a heart rate sensor, a blood pressure sensor, a blood sugar sensor, a perspiration sensor, a skin conductivity sensor, or an imaging sensor. The device may process the sensor data, from the plurality of types of sensors, relating to the user to determine a health condition of the user. The device may provide, via a user interface, information identifying the health condition of the user based on processing the sensor data, from the plurality of types of sensors, relating to the user.

20 Claims, 10 Drawing Sheets

Related U.S. Application Data continuation of application No. 15/135,110, filed on Apr. 21, 2016, now Pat. No. 10,251,597.

(51) Int. Cl.

| | | |
|---|---|---|
| *A61B 5/11* | (2006.01) | |
| *A61B 5/145* | (2006.01) | |
| *G01N 21/27* | (2006.01) | |
| *G01N 33/02* | (2006.01) | |
| *G06F 3/04842* | (2022.01) | |
| *G16H 20/30* | (2018.01) | |
| *G16H 20/60* | (2018.01) | |
| *G16H 40/63* | (2018.01) | |
| *G16H 40/67* | (2018.01) | |
| *G16H 50/20* | (2018.01) | |
| *A61B 5/021* | (2006.01) | |
| *A61B 5/024* | (2006.01) | |
| *A61B 5/0531* | (2021.01) | |

(52) U.S. Cl.
CPC ........ *A61B 5/1118* (2013.01); *A61B 5/14532* (2013.01); *A61B 5/4266* (2013.01); *A61B 5/486* (2013.01); *A61B 5/4866* (2013.01); *A61B 5/6801* (2013.01); *A61B 5/7278* (2013.01); *A61B 5/746* (2013.01); *A61B 5/747* (2013.01); *G01N 21/27* (2013.01); *G01N 33/02* (2013.01); *G06F 3/04842* (2013.01); *G16H 20/60* (2018.01); *G16H 40/63* (2018.01); *G16H 40/67* (2018.01); *G16H 50/20* (2018.01); *A61B 5/021* (2013.01); *A61B 5/02438* (2013.01); *A61B 5/0531* (2013.01); *A61B 2562/0219* (2013.01)

(58) Field of Classification Search
CPC ........ A61B 2560/0223; A61B 2503/40; A61B 5/6831; A61B 5/076; A61B 5/1121; A61B 2560/0214; A01K 29/005
See application file for complete search history.

(56) References Cited

U.S. PATENT DOCUMENTS

| | | |
|---|---|---|
| 2003/0208113 A1 | 11/2003 | Mault et al. |
| 2004/0117212 A1 | 6/2004 | Kong et al. |
| 2004/0204868 A1 | 10/2004 | Maynard et al. |
| 2008/0294013 A1 | 11/2008 | Gobeyn et al. |
| 2012/0059664 A1 | 3/2012 | Georgiev et al. |
| 2014/0240124 A1 | 8/2014 | Bychkov |
| 2014/0320858 A1 | 10/2014 | Goldring et al. |
| 2014/0347491 A1* | 11/2014 | Connor ................. A61B 5/1114 348/158 |
| 2015/0169847 A1* | 6/2015 | McKinney ........... G01N 21/359 703/12 |
| 2015/0262497 A1 | 9/2015 | Landau et al. |
| 2015/0300969 A1* | 10/2015 | Grosman ............. G01N 27/026 204/403.01 |
| 2015/0356701 A1 | 12/2015 | Gandy et al. |
| 2016/0015301 A1 | 1/2016 | Elliott et al. |
| 2016/0071423 A1 | 3/2016 | Sales et al. |
| 2017/0024885 A1 | 1/2017 | Miyazaki |
| 2017/0220772 A1* | 8/2017 | Vleugels ............... A61B 5/0022 |
| 2019/0223780 A1 | 7/2019 | O'Brien et al. |

FOREIGN PATENT DOCUMENTS

| | | |
|---|---|---|
| CN | 204613090 U | 9/2015 |
| CN | 105307568 A | 2/2016 |
| CN | 105393252 A | 3/2016 |
| JP | 2013092372 A | 5/2013 |
| JP | 2013092917 A | 5/2013 |
| JP | 2014074976 A | 4/2014 |
| JP | 2015204033 A | 11/2015 |
| WO | 0205702 A2 | 1/2002 |
| WO | 2012094569 A2 | 7/2012 |
| WO | 2015101992 A2 | 7/2015 |
| WO | 2016037091 A1 | 3/2016 |

OTHER PUBLICATIONS

Extended European Search Report for Application No. EP17167432, mailed on Oct. 2, 2017, 13 pages.
Langheinrich M., et al., "Unintrusive Customization Techniques for Web Advertising," 1999, 14 pages.
Nield D., "How it Works: We Explain How your Fitness Tracker Measures your Daily Steps," Jul. 28, 2015, 4 pages.
Pierna F., et al., "Combination of Support Vector Machines (SVM) and Near-Infrared (NIR) Imaging Spectroscopy for the Detection of Meat and Bone Meal (MBM) in Compound Feeds," Journal of Chemometrics, vol. 18(7-8), Dec. 21, 2004, pp. 341-349.

* cited by examiner

HEALTH TRACKING DEVICE

RELATED APPLICATIONS

This application is a continuation of U.S. patent application Ser. No. 16/375,221, filed Apr. 4, 2019 (now U.S. Pat. No. 10,950,335), which is a continuation of U.S. patent application Ser. No. 15/135,110, filed Apr. 21, 2016 (now U.S. Pat. No. 10,251,597), which are incorporated herein by reference.

BACKGROUND

A wearable fitness tracker may perform a measurement of user activity based on sensor data received from a sensor. For example, the wearable fitness tracker may include an accelerometer that provides sensor data to estimate user activity during an exercise session. The wearable fitness tracker may provide, for display, information associated with the user activity during the exercise session. For example, the wearable fitness tracker may estimate one or more metrics, such as an estimated distance traveled, an estimated calorie consumption metric, an estimated metabolic equivalents (METs) metric, or the like, based on the sensor data from the accelerometer and may provide the one or more metrics for display.

SUMMARY

According to some possible implementations, a device may include one or more processors. The one or more processors may receive, from a plurality of sensors, sensor data relating to a user. The plurality of sensors may include a plurality of types of sensors including a spectrometer and one or more of an accelerometer, a heart rate sensor, a blood pressure sensor, a blood sugar sensor, a perspiration sensor, a skin conductivity sensor, or an imaging sensor. The one or more processors may process the sensor data, from the plurality of types of sensors, relating to the user to determine a health condition of the user. The one or more processors may provide, via a user interface, information identifying the health condition of the user based on processing the sensor data, from the plurality of types of sensors, relating to the user.

According to some possible implementations, a non-transitory computer-readable medium may store one or more instructions that, when executed by one or more processors, may cause the one or more processors to receive a first spectroscopic classification model. The first spectroscopic classification model may be associated with identifying a health condition based on a chemometric signature. The first spectroscopic classification model may be generated based on a calibration performed utilizing a spectrometer on a group of subjects. The one or more instructions, when executed by one or more processors, may cause the one or more processors to obtain a set of properties regarding a user. The set of properties including first sensor data regarding the user. The one or more instructions, when executed by one or more processors, may cause the one or more processors to generate a second spectroscopic classification model based on the first spectroscopic classification model and the set of properties regarding the user. The second spectroscopic classification model may permit a determination of a characteristic of the user or a food item. The one or more instructions, when executed by one or more processors, may cause the one or more processors to periodically update the second spectroscopic classification model based on second sensor data regarding the user.

According to some possible implementations, a method may include determining, by a device, an activity level of a user based on first sensor data relating to the activity level of the user from a first set of sensors. The method may include determining, by the device, a nutritional content of a set of food items for consumption by the user based on second sensor data relating to the nutritional content of the set of food items from a second set of sensors. The second sensor data may be obtained from a spectrometer. The method may include obtaining, by the device, a stored diet and exercise plan for the user. The stored diet and exercise plan may include a goal relating to the activity level of the user and the nutritional content of the set of food items for consumption by the user. The method may include determining, by the device, a user compliance with the stored diet and exercise plan based on the activity level of the user and the nutritional content of the set of food items. The method may include providing, by the device, a recommendation relating to user compliance with the stored diet and exercise plan based on determining the user compliance with the stored diet and exercise plan.

DETAILED DESCRIPTION

The following detailed description of example implementations refers to the accompanying drawings. The same reference numbers in different drawings may identify the same or similar elements.

A wearable fitness tracker may utilize a set of accelerometers to obtain sensor data regarding user activity. For example, the wearable fitness tracker may determine an estimated distance traveled by a user based on sensor data identifying a movement of the wearable fitness tracker. The wearable fitness tracker may include information that may be utilized to estimate one or more metrics relating to user activity. For example, the wearable fitness tracker may estimate a calorie expenditure based on the estimated distance traveled and generic information correlating distance traveled to calorie expenditure for a generic person.

However, utilizing generic correlations to determine the one or more metrics may result in an inaccurate calculation for a particular user. Moreover, the wearable fitness tracker may fail to account for factors, other than exercise, that affect health of a user, such as nutrition, mood, illness, or the like, thereby limiting a usefulness of the wearable fitness tracker. Implementations, described herein, may utilize sensor data associated with multiple sensors to provide health information associated with a user. In this way, a single user device may determine the health information for a user, obviating the need for the user to utilize multiple different devices, thereby reducing cost, power consumption, or the like relative to utilizing the multiple different devices for health tracking. Moreover, the user device may utilize the sensor data from the multiple sensors to facilitate calibration of a model for spectroscopic analysis, thereby improving accuracy of the model relative to utilizing a model that is not calibrated based on sensor data from other sensors.

Figure 1:
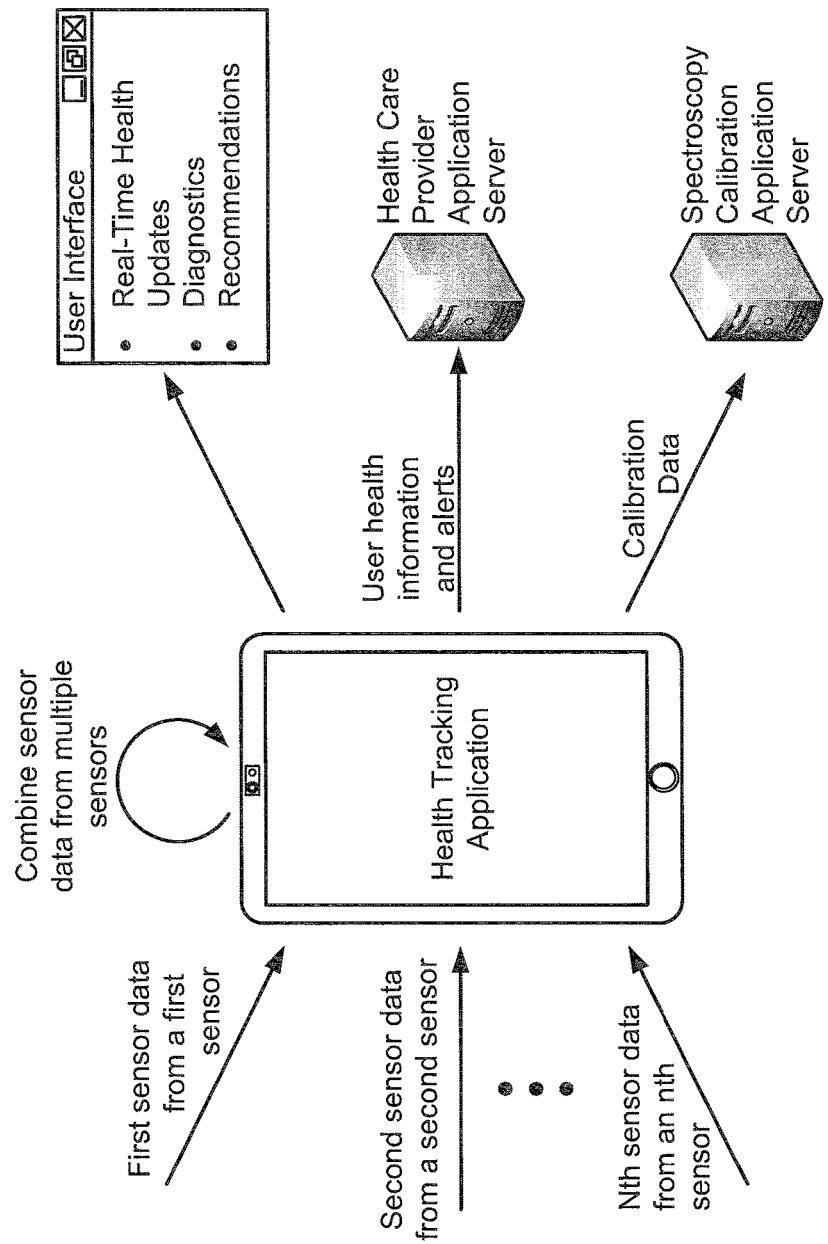
FIG. 1 is a diagram of an overview of an example implementation described herein.

FIG. 1 is a diagram of an overview of an example implementation 100 described herein. As shown in FIG. 1, example implementation 100 includes a user device, a health care provider application server, and a spectroscopy calibration application server.

As further shown in FIG. 1, the user device may receive sensor data from multiple sensors (e.g., first sensor data from a first sensor, second sensor data from a second sensor, ..., and nth sensor data from an nth sensor). For example, the user device 210 may utilize a set of integrated sensors to obtain the sensor data, such as an integrated accelerometer sensor to obtain user activity data, an integrated heart rate sensor to obtain heart rate data, an integrated temperature sensor to obtain temperature data, or the like. Additionally, or alternatively, the user device may utilize a camera to obtain the sensor data. For example, the user device may utilize an integrated camera to capture an image, such as an image of a user's face (e.g., for a facial recognition analysis), an image of the user's skin (e.g., for a skin condition analysis), a set of images of food (e.g., a set of images for performing a volumetric analysis of the food), or the like. Additionally, or alternatively, the user device may utilize a spectroscopic sensor to obtain the sensor data. For example, the user device may utilize the spectroscopic sensor to determine a chemometric signature for a subject (e.g., the user or an item of food), and may classify the subject based on the chemometric signature and a classification model. In another example, the user device may communicate with one or more sensors to obtain sensor data. For example, the user device may utilize a connection to a medical device to obtain sensor data recorded by the medical device.

As further shown in FIG. 1, the user device may combine the sensor data from the multiple sensors to generate health information regarding the user. For example, based on sensor data regarding a user activity level, a user heart rate, a user body temperature, or the like and stored information regarding a user height, a user weight, or the like, the user device may determine a calorie expenditure by the user associated with an exercise program. Based on utilizing information in addition to accelerometer data (e.g., the user heart rate data and/or the user body temperature data), the user device may obtain a more accurate determination of the calorie expenditure than based on only utilizing the accelerometer data.

Similarly, based on image sensor data and spectroscopic sensor data, the user device may determine, respectively, a volume of a food item and a nutritional content of the food item. Based on utilizing the spectroscopic sensor data identifying a composition of the food item and the sensor data identifying a volume of the food item, the user device may obtain a more accurate determination of calorie intake by the user than based on utilizing a user estimation of nutritional value. Based on the calorie expenditure determination and the calorie intake determination, the user device may determine a net calorie consumption for a user, and may generate a recommendation associated with the net calorie consumption, such as a nutritional recommendation, an exercise recommendation, or the like to improve user health and/or user compliance with a diet and exercise plan. In this way, the user device performs determinations relating to health of the user that are more accurate than determinations performed by a wearable fitness tracker, thereby permitting improved fitness tracking.

As another example, the user device may process the sensor data to determine diagnostic information regarding a user. For example, based on performing a pattern recognition analysis on an image of the user, the user device may detect facial redness and pimples associated with a rosacea condition. Similarly, based on performing a pattern recognition analysis on an image of the user, the user device may determine that the user is in a comfort state, and may correlate the comfort state with other sensor data, such as sensor data indicating that the user was previously eating a particular item of food. In this case, the user device may periodically provide a recommendation relating to altering a mood of the user, such as a recommendation that the user eat the particular item of food that correlates with a comfort state.

As another example, the user device may process spectroscopic sensor data to calibrate a classification model for spectroscopy. For example, the user device may utilize a first model to perform a first classification of first spectroscopic sensor data, such as to classify an observed chemometric signature as relating to a particular person with a particular blood pressure and after eating a particular food item. In this case, the user device may calibrate the first model to generate a second model based on the first spectroscopic sensor data and other sensor data (e.g., sensor data identifying the particular blood pressure and the particular food item), and may utilize the second model to perform another classification of second spectroscopic sensor data. For example, the user device may utilize the second classification model to distinguish between the particular person when the particular person is associated with the particular blood pressure and the particular person when the particular person is associated with another blood pressure. In this way, the user device refines a classification model to perform spectroscopy with improved accuracy relative to a classification model that is not refined based on other sensor data.

As further shown in FIG. 1, the user device may provide information, such as health information relating to the user, diagnostic information relating to a health condition of the user, recommendations relating to improving user health and/or compliance with a diet and exercise plan, or the like based on processing the sensor data from the multiple sensors. Compliance with a diet and exercise plan may be associated with reducing a severity of a health condition (e.g., a heart disease condition or an obesity condition), managing symptoms of a health condition (e.g., a diabetes health condition or a stress condition), reducing a likelihood of deterioration of a health condition (e.g., a degenerative condition), achieving a desired health condition (e.g., improving diet, increasing an intake of whole grains, increasing muscle mass, or improving an athletic performance). For example, the user device may provide, for display via a user interface, a real-time health update, such as information indicating a net calorie consumption based on the calorie expenditure and the calorie intake determinations. Additionally, or alternatively, the user device may provide diagnostic information indicating that a particular condition is detected for the user, and may automatically transmit data to a specialist to establish an appointment for the user with the specialist. Additionally, or alternatively, the user device may generate a recommendation, such as a recommendation for an exercise regimen to permit the user to comply with a diet and exercise plan, and may provide updates regarding user compliance with the diet and exercise plan for display via another device (e.g., a user device utilized by a personal trainer or a nutritionist). In this way, the user device provides information customized to the user rather than generic information.

As further shown in FIG. 1, the user device may provide health information to a health care provider application server for inclusion in a patient file relating to the user. In this way, the user device improves doctor patient consultations by improving data accuracy relative to a doctor relying on manual patient reporting of diet, exercise, or the like and reducing a utilization of processing resources and/or a power consumption relative to providing one or more user interfaces for receiving input of patient reporting and/or correcting the input of the patient reporting. Additionally, or alternatively, the user device may provide calibration data to a spectroscopy calibration application server. For example, the user device may provide calibration information determined from a spectroscopic sensor and/or other sensors for utilization in calibrating and/or refining a classification model that is provided to one or more other user devices, thereby improving accuracy of spectroscopy for the one or more other user devices relative to the one or more other user devices receiving a model not calibrated based on the calibration information.

In this way, the user device provides health information determined based on sensor data obtained from multiple sensors, thereby reducing cost and power consumption relative to the user utilizing multiple different devices. Moreover, based on integrating the sensor data collection and processing into a single user device, the user device permits determination of health information that is not obtainable via a single sensor, such as obtaining nutrition information based on both a volumetric analysis and a spectroscopic analysis or the like. Furthermore, the user device improves calibration of a classification model for spectroscopic analysis based on performing model calibration and model refinement based on both spectroscopic data and other sensor data regarding a subject of spectroscopic analysis relative to a single initial calibration via a single device.

As indicated above, FIG. 1 is provided merely as an example. Other examples are possible and may differ from what was described with regard to FIG. 1.

Figure 2:
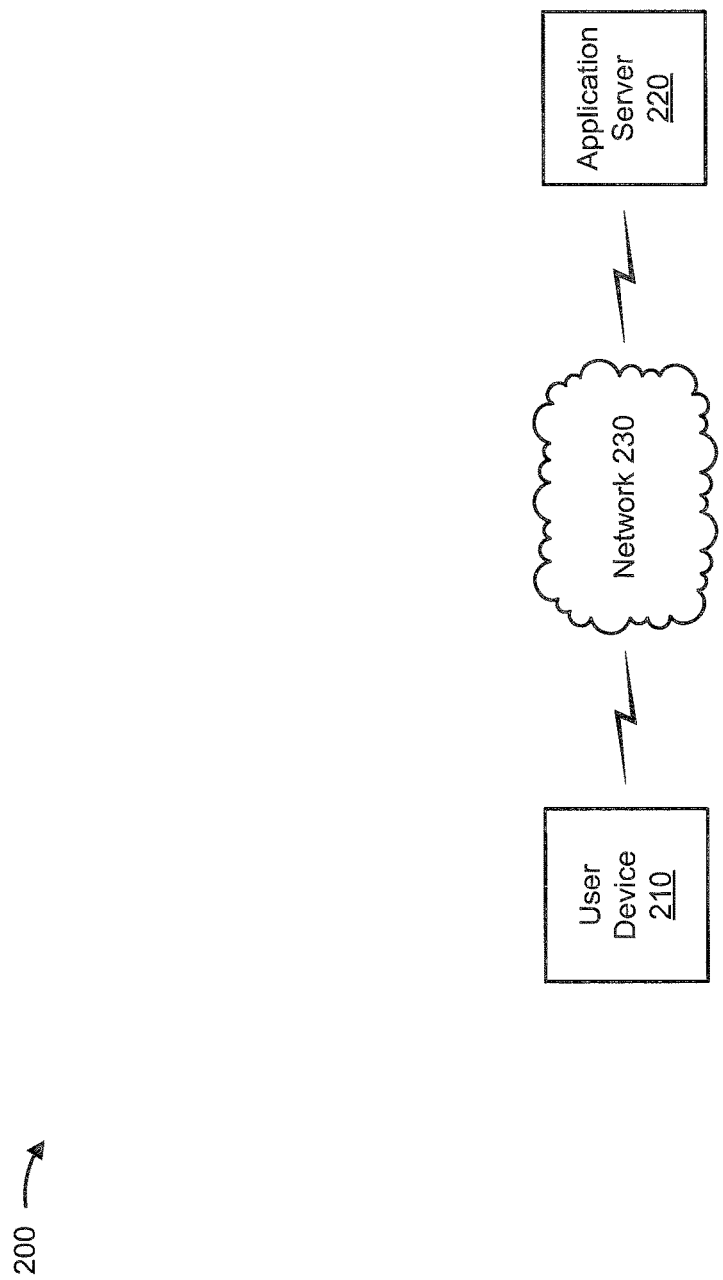
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, an application server 220, and a network 230. Devices of environment 200 may interconnect via wired connections, wireless connections, or a combination of wired and wireless connections.

User device 210 includes one or more devices capable of receiving, generating, storing, processing, and/or providing health information. For example, user device 210 may include a communication and/or computing device, such as a mobile phone (e.g., a smart phone, a radiotelephone, etc.), a laptop computer, a tablet computer, a handheld computer, a gaming device, a wearable device (e.g., a smart wristwatch, a pair of smart eyeglasses, a smart wristband, etc.), a medical device, a spectroscopic device (e.g., a wearable spectrometer device that performs near infrared (NIR) spectroscopy, mid-infrared (mid-IR) spectroscopy, or Raman spectroscopy), or a similar type of device. In some implementations, the spectroscopic device may include a hyperspectral spectrometer (e.g., a hyperspectral imaging sensor). In some implementations, user device 210 may receive information from and/or transmit information to another device in environment 200.

Application server 220 includes one or more devices capable of storing, processing, and/or routing information, such as health information, calibration information, or the like. For example, application server 220 may include a server that utilizes health information and/or information associated with user device 210. In some implementations, application server 220 may include a calibration application server 220 that receives information associated with calibration of a spectroscopic model based on a set of measurements performed by one or more user devices 210. Additionally, or alternatively, application server 220 may include a health care provider application server 220 associated with routing information for a health care provider, such as a hospital server or the like. In some implementations, application server 220 may receive information from and/or transmit information to another device in environment 200.

Network 230 includes one or more wired and/or wireless networks. For example, network 230 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
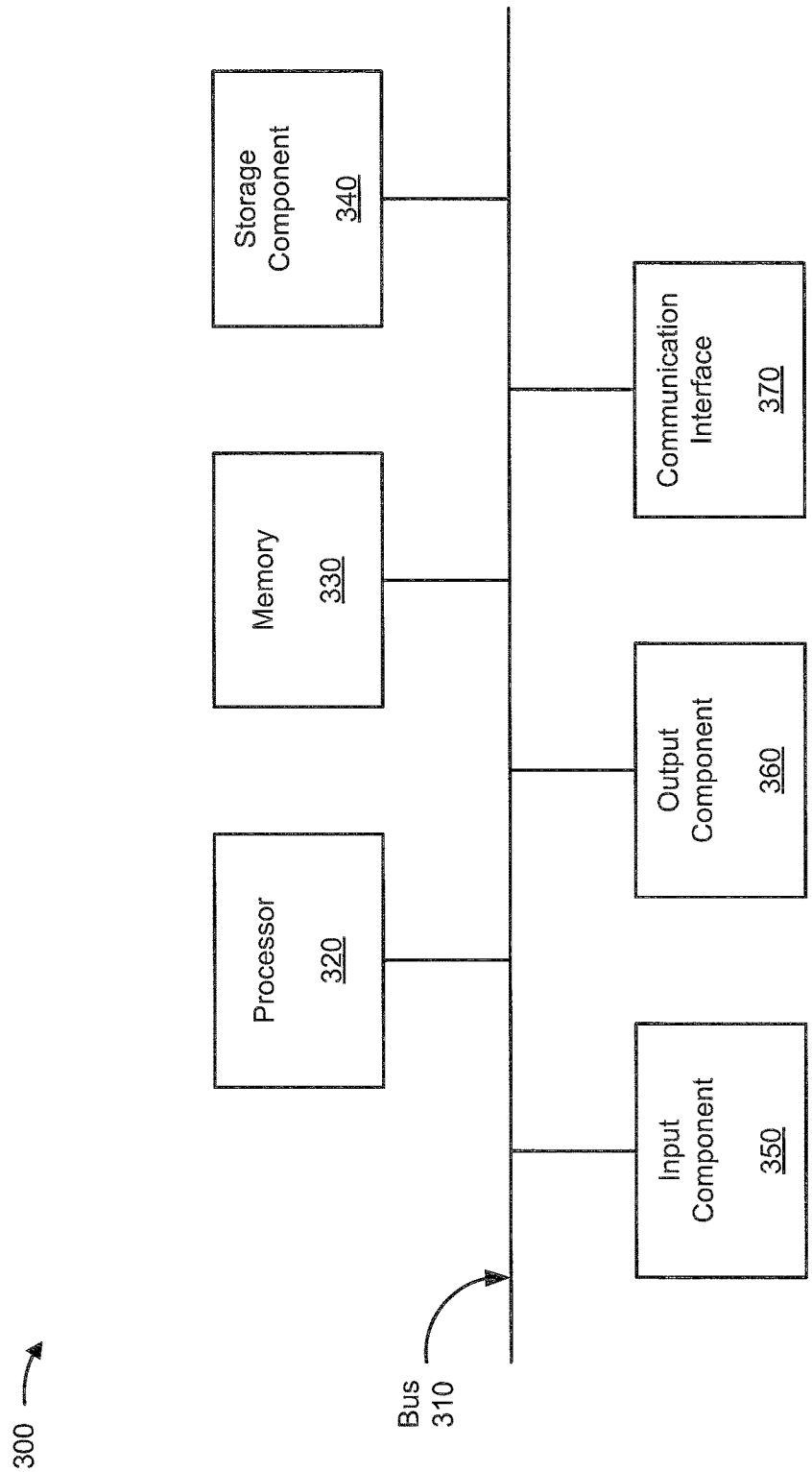
FIG. 3 is a diagram of example components of one or more devices of FIG. 2.

FIG. 3 is a diagram of example components of a device 300. Device 300 may correspond to user device 210 and/or application server 220. In some implementations, user device 210 and/or application server 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. In some implementations, processor 320 may include one or more processors capable of being programmed to perform a function. Memory 330 includes a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 includes a component that provides output information from device 300 (e.g., a display, a speaker, one or more light-emitting diodes (LEDs), etc.).

Communication interface 370 includes a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
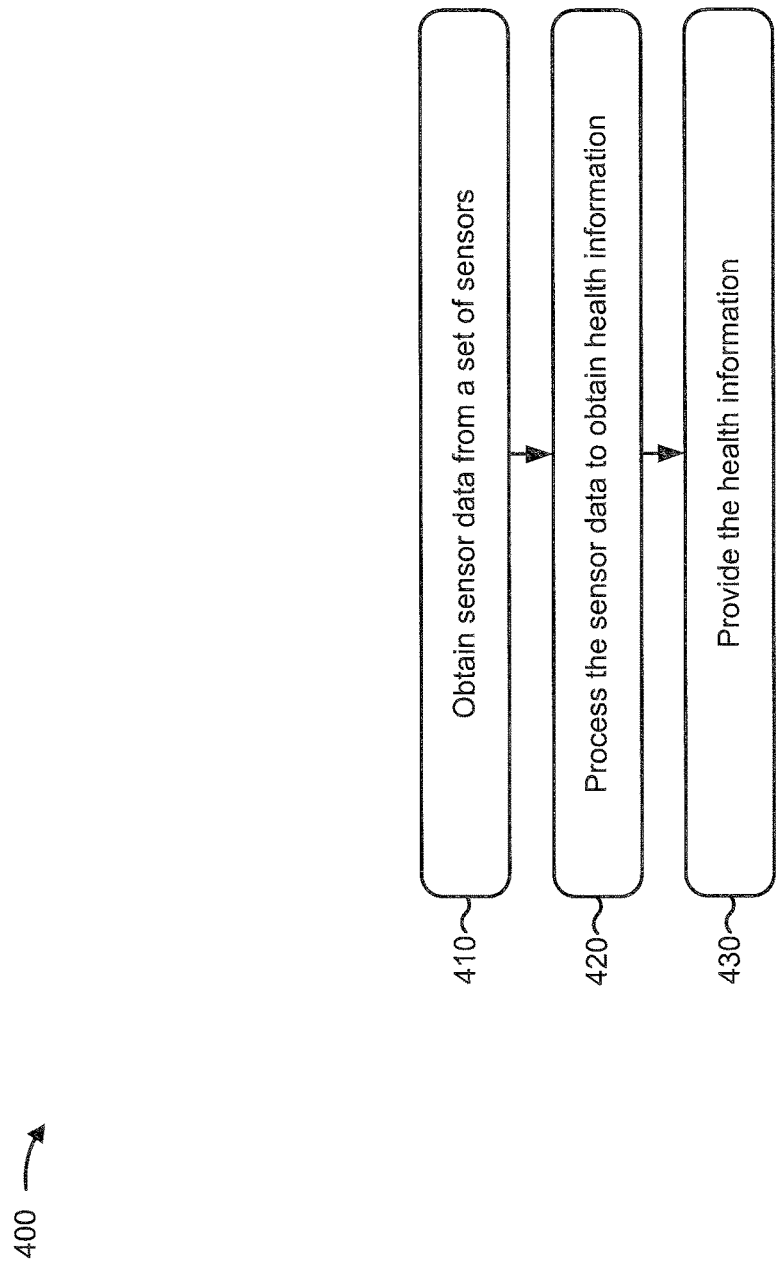
FIG. 4 is a flow chart of an example process for providing health information based on sensor data associated with multiple sensors.

FIG. 4 is a flow chart of an example process 400 for providing health information based on sensor data associated with multiple sensors. In some implementations, one or more process blocks of FIG. 4 may be performed by user device 210. In some implementations, one or more process blocks of FIG. 4 may be performed by another device or a group of devices separate from or including user device 210, such as application server 220 or the like.

As shown in FIG. 4, process 400 may include obtaining sensor data from a set of sensors (block 410). For example, user device 210 may obtain sensor data from the set of sensors of user device 210. In some implementations, user device 210 may obtain the sensor data based on communicating with the set of sensors. For example, user device 210 may cause a heartbeat sensor of user device 210 to activate and record sensor data regarding a heartbeat of a user. Similarly, user device 210 may cause an accelerometer sensor of user device 210 to activate and record accelerometer sensor data regarding movement of user device 210 (e.g., activity of a user using user device 210).

In some implementations, user device 210 may obtain the sensor data based on providing a prompt via a user interface. For example, user device 210 may provide a prompt to cause a user to utilize user device 210 to capture an image of the user (e.g., a photograph of the user's face or a photograph of a portion of the user's skin). Additionally, or alternatively, user device 210 may provide a prompt to cause the user to utilize user device 210 to capture an image of an item of food. For example, user device 210 may be utilized to capture an image of a meal, and may process the image of the meal to identify a nutritional content of the meal. Additionally, or alternatively, user device 210 may capture an image automatically. For example, user device 210 may determine that a meal is prepared, such as based on a time of day, based on location data indicating that user device 210 is at a restaurant, based on social media information indicating that user device 210 is at a restaurant, or the like, and may automatically activate an imaging sensor to capture an image. Similarly, user device 210 may determine, based on an accelerometer, based on a touch sensor, or the like, that an imaging sensor of user device 210 is directed toward the user, and may cause the imaging sensor to capture an image of the user.

In some implementations, user device 210 may monitor an imaging sensor to obtain sensor data. For example, user device 210 may perform an object recognition technique on a set of images captured via the imaging sensor to determine whether the set of images captured include information utilizable for providing a health report, such as determining that a particular image includes a food item, determining that the particular image includes the user, or the like. In this case, user device 210 may select the particular image for processing (e.g., a volumetric analysis processing technique, a mood analysis processing technique, or a skin condition processing technique).

In some implementations, user device 210 may obtain the sensor data based on a trigger. For example, user device 210 may detect a user interaction with a user interface, and may be caused to obtain the sensor data. Additionally, or alternatively, user device 210 may obtain the sensor data periodically. For example, based on determining that a threshold period of time has elapsed (e.g., an hour, a day, or a week), user device 210 may obtain the sensor data. Similarly, at a particular time of day, user device 210 may obtain the sensor data. In some implementations, user device 210 may obtain the sensor data based on other sensor data. For example, user device 210 may detect that a user has finished an exercise regimen based on monitoring a heart rate sensor (e.g., based on heart rate sensor data), and may obtain other sensor data based on determining that the user has finished the exercise regimen. Similarly, user device 210 may identify the user based on chemometric signature sensor data from a spectrometer sensor, and may obtain other sensor data based on identifying the user.

As further shown in FIG. 4, process 400 may include processing the sensor data to obtain health information (block 420). For example, user device 210 may process the sensor data to obtain the health information. In some implementations, user device 210 may process the sensor data to identify one or more metrics related to user health. For example, user device 210 may determine an activity level metric based on sensor data associated with multiple types of sensors, such as an accelerometer, a heart rate sensor, a skin temperature sensor, a blood pressure sensor, or the like. Similarly, user device 210 may determine a nutrition metric based on sensor data associated with a blood pressure sensor, a blood sugar sensor, a perspiration sensor, a skin conductivity sensor, or the like.

In some implementations, user device 210 may utilize a particular processing technique to process the sensor data. For example, user device 210 may utilize a classification technique associated with a classification model to identify content of a food item based on a spectroscopic measurement (e.g., a chemometric signature), and may determine health information related to food consumption based on identifying the content of the food item. In some implementations, user device 210 may perform the classification based on sensor data received from a hyperspectral spectrometer, which may user difficulty and errors related to distance from the subject relative to utilizing another type of sensor. Additionally, or alternatively, user device 210 may apply a pattern detection technique, a facial recognition technique, a three-dimensional depth sensing technique, or the like to an image of a user to determine a user mood, a level of fatigue, a level of stress, a migraine symptom, a skin condition, or the like. Additionally, or alternatively, user device 210 may utilize a color classification technique to determine that a color of urine in an image corresponds to a particular health condition, such as insufficient or excessive consumption of a particular vitamin (e.g., a B-vitamin deficiency) or the like.

Additionally, or alternatively, user device 210 may utilize a volumetric analysis technique to process the sensor data. For example, user device 210 may utilize a set of images of a food item (e.g., a set of images captured from different orientations and/or positions), to determine a volume of the food item. Additionally, or alternatively, user device 210 may utilize sensor data captured by a depth sensing module, a gesture recognition module, or the like to perform the volumetric analysis. In some implementations, user device 210 may determine a food item mass based on the volumetric analysis. For example, user device 210 may utilize information identifying a density of the food item (e.g., sensor data, image recognition of the food item, or a user selection of the food item and corresponding stored food item density data), and may determine a mass for the food based on the density (e.g., which may be utilized to determine a nutritional content of the food based on a spectroscopic analysis indicating a nutritional content on a per mass basis). Additionally, or alternatively, user device 210 may utilize a set of images of a user to determine a volume of a portion of the user, such as a volume of a shoulder hump, a skin bump, or the like. In this way, user device 210 identifies a volume of a subject for comparison with the subject at another time, to determine a nutritional content of the subject (e.g., with other sensor data identifying a type of food item that is the subject), or the like.

In some implementations, user device 210 may process the sensor data using a comparison technique, such as comparing first sensor data recorded at a first time to second sensor data recorded at a second time. For example, user device 210 may compare a first three-dimensional image of a user at a first time period with a second three-dimensional image of the user at a second time period to identify changes to the user's appearance, such as growth of a mole (e.g., corresponding to tumor growth), change to a breast shape (e.g., corresponding to cyst growth), change to a body shape (e.g., corresponding to a weight gain), change to a chemometric signature (e.g., corresponding to a change in blood composition associated with a diabetes type disorder), or the like.

As further shown in FIG. 4, process 400 may include providing the health information (block 430). For example, user device 210 may provide the health information. In some implementations, user device 210 may provide, via a user interface, a health report for review by a user. For example, user device 210 may provide a report including health information identifying a net calorie consumption (e.g., a comparison of calorie intake and calorie expenditure) for the user. Additionally, or alternatively, user device 210 may provide information identifying a portion of sensor data processed by user device 210, such as a set of vital statistics determined for the user (e.g., a blood pressure, a body temperature, a heart rate, or a perspiration level).

In some implementations, user device 210 may provide a recommendation based on the sensor data. For example, user device 210 may determine a set of health recommendations (e.g., to improve an obesity condition, to manage a diabetes condition, to prevent a degenerative condition, to improve an athletic performance, or to satisfy a nutrition goal), may select a particular health recommendation of the set of health recommendations (e.g., that the user consume a particular quantity of calories during a particular meal based on a metabolic rate of the user), and may provide health information including the particular health recommendation for display via a user interface. Additionally, or alternatively, user device 210 may select another health recommendation (e.g., that the user is predicted to experience improved mood levels based on consuming a particular food or engaging in a particular exercise regimen), and may provide the other health recommendation for display via another user device 210 (e.g., that is utilized by a physician, a life coach, a trainer, or a personal chef).

In some implementations, user device 210 may provide an alert based on the sensor data. For example, user device 210 may provide, based on sensor data identifying a health condition of the user, a particular alert identifying the health condition for display via the user interface. In this case, the alert may identify the health condition, a severity of the health condition, or the like. Additionally, or alternatively, user device 210 may provide an alert for display via another user device 210. For example, user device 210 may identify a specialist doctor associated with the health condition, and may transmit an alert for display via another user device 210 that is utilized by the specialist doctor. Similarly, user device 210 may transmit an alert to cause emergency management personnel to be dispatched for the user. For example, when user device 210 determines that a severity of the health condition satisfies a threshold severity, user device 210 may utilize a location determination technique to determine a location of the user, and may transmit an alert to an ambulance dispatch, a hospital, or the like to cause emergency management personnel to be dispatched to the location of the user. In some implementations, user device 210 may provide a health report when providing the alert. For example, user device 210 may provide information identifying a blood pressure of the user, a heart rate of the user, a body temperature of the user, or the like for utilization by a doctor, by emergency management personnel, or the like.

In some implementations, user device 210 may provide calibration data. For example, when user device 210 transmits spectroscopic data regarding a user for calibrating a model, user device 210 may provide health information regarding the user for calibrating the model. In this case, the health information may be utilized to calibrate the model to a particular health condition (e.g., a first chemometric signature may be determined to correspond to a first perspiration level and a second chemometric signature may be determined to correspond to a second perspiration level).

In some implementations, user device 210 may provide, for display, an augmented reality image based on the sensor data. For example, when user device 210 determines a caloric content of a food item based on images of the food item, user device 210 may determine a portion of the food item that, when consumed, corresponds to satisfying a nutrition goal. In this case, user device 210 may provide, for display, an image of the food item with the portion of the food item highlighted, an augmented reality display of the food item with the portion of the food item highlighted, or the like. In this way, a user may be provided information indicating how much of a food item to consume to satisfy a nutrition goal.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5D are diagrams of an example implementation 500 relating to example process 400 shown in FIG. 4. FIGS. 5A-5D show an example of providing health information based on sensor data associated with multiple sensors.

Figure 5A:
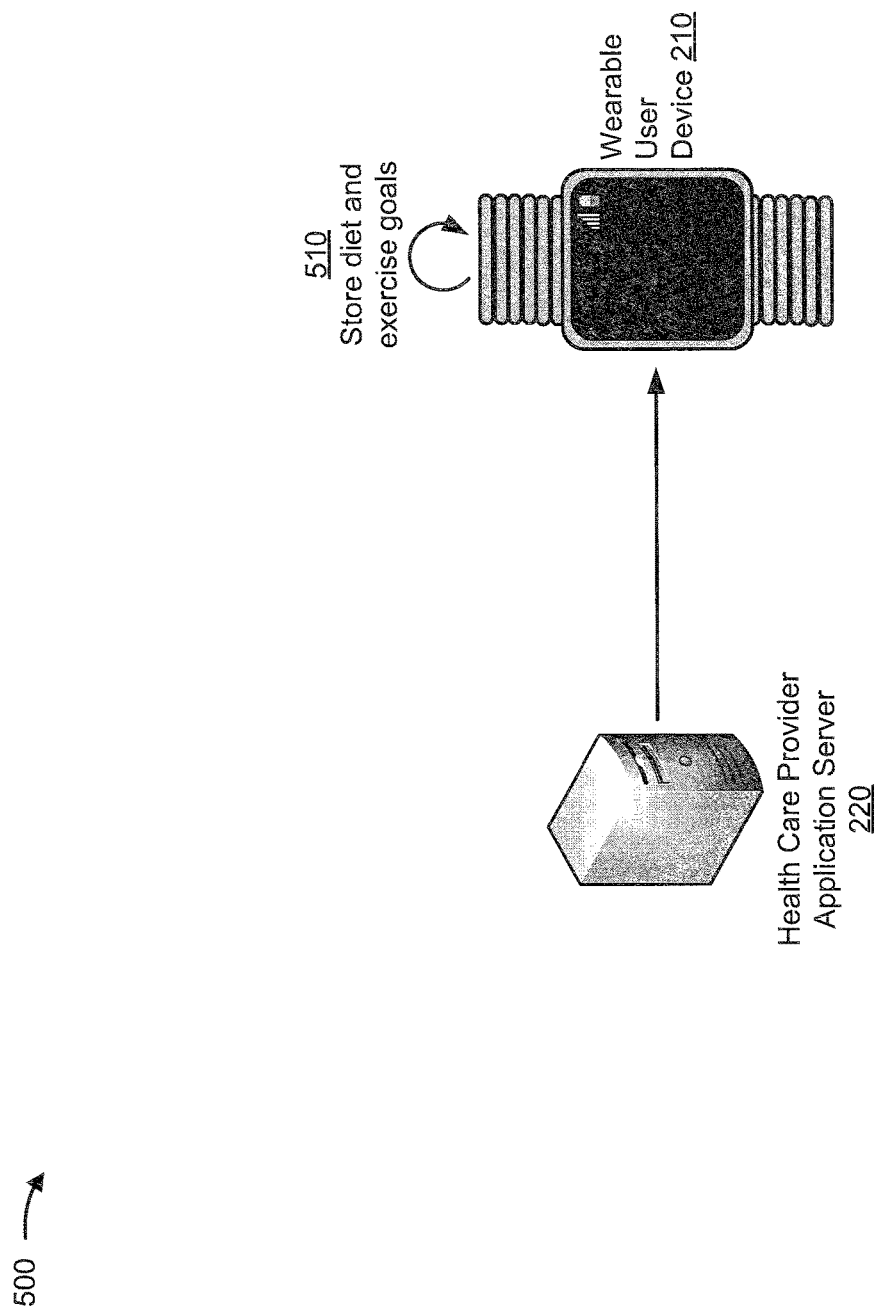
FIGS. 5A-5D are diagrams of an example implementation relating to the example process shown in FIG. 4.

As shown in FIG. 5A, and by reference number 510, a wearable user device 210 (e.g., a smart watch including a set of sensors) may store a set of diet and exercise goals received from a health care provider application server 220. For example, the set of diet and exercise goals may be generated based on a user consultation with a health care provider (e.g., a doctor, a personal trainer, or a nutritionist), and may be transmitted to wearable user device 210 to permit wearable user device 210 to monitor user diet and exercise to determine and improve compliance with the set of diet and exercise goals. Assume that the set of diet and exercise goals includes a diet goal associated with the user having an intake of a threshold amount of carbohydrates in a day, an exercise goal associated with the user satisfying a threshold physical activity level during the day, and a combined diet and exercise goal associated with the user satisfying a threshold net calorie consumption (e.g., a greater calorie expenditure than calorie intake during the day).

Figure 5C:
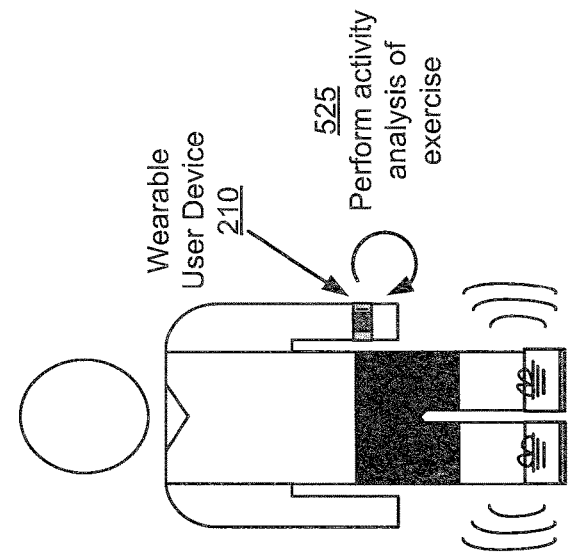
Figure 5B:
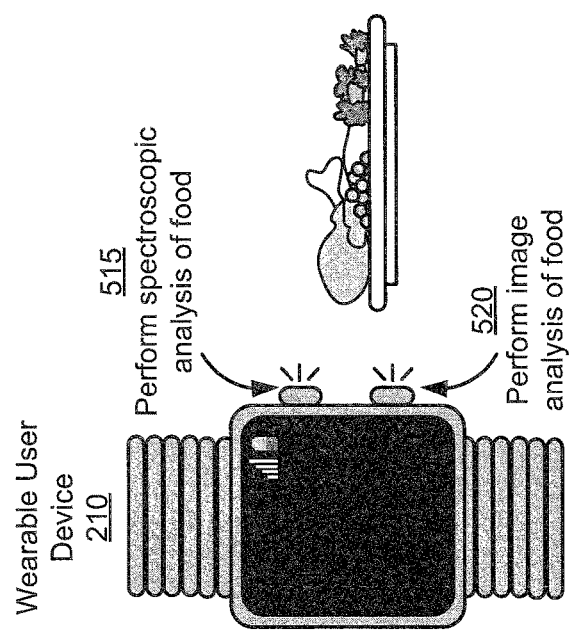

As shown in FIG. 5B, and by reference number 515, wearable user device 210 performs a spectroscopic analysis of a food item to determine a content of the food item, such as a protein content, a fat content, or a carbohydrate content using data from a spectroscopic sensor. As shown by reference number 520, wearable user device 210 performs an image analysis of food item to determine a volume of the food item using a set of images from an imaging sensor. Assume that wearable user device 210 determines a carbohydrate intake and a calorie intake for the user based on the content of the food item (e.g., the spectroscopic analysis indicating the content of the food) and the volume of the food item (e.g., the volumetric analysis indicating the content of the food). Assume that based on the carbohydrate intake, wearable user device 210 provides information via the user interface indicating compliance with the diet goal, such as an alert indicating an amount of carbohydrates that the user is permitted to consume during the remainder of the day.

As shown in FIG. 5C, and by reference number 525, wearable user device 215 performs an activity analysis of a user exercise regimen using data from a heart rate sensor, an accelerometer sensor, or the like. Assume that wearable user device 210 determines a calorie expenditure and a physical activity level based on performing the activity analysis of the user exercise regimen. Assume that based on the physical activity level, wearable user device 210 provides information via the user interface indicating compliance with the exercise goal, such as information indicating that the user satisfied the threshold physical activity level for the day.

Figure 5D:
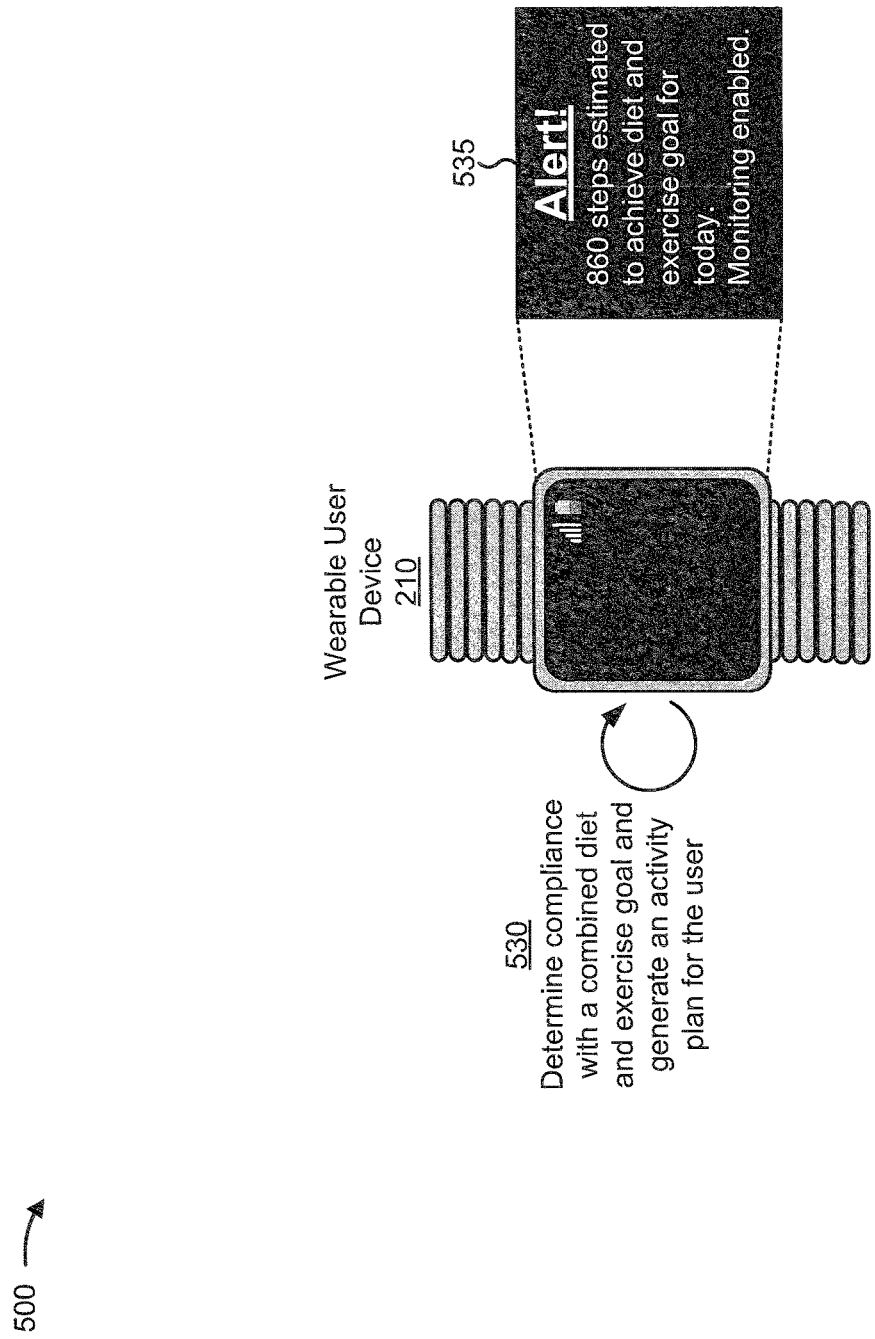

As shown in FIG. 5D, and by reference number 530, wearable user device 210 determines compliance with the combined diet and exercise goal and generates an activity plan for the user associated with causing the user to perform a particular activity (e.g., a particular quantity of steps) associated with a corresponding alteration to sensor data associated with the user (e.g., causing the sensor data to indicate that user calorie expenditure has increased for the day). Assume that wearable user device 210 determines that the user has failed to satisfy the combined diet and exercise goal based on the calorie intake for the user exceeding the calorie expenditure by the user. Further assume that wearable user device 210 determines that based on previous activity by the user, walking a particular quantity of steps by the user before the end of the day corresponds to achieving the combined diet and exercise goal. As shown by reference number 535, wearable user device 210 provides an alert indicating that the user is to walk the particular quantity of steps before the end of the day, and continues to monitor user activity and provide alerts to cause the user to walk the particular quantity of steps. In this way, wearable user device 210 improves compliance with the combined diet and exercise goal relative to a step counter device that only provides information indicating steps take and estimated calorie expenditure without including other data and without comparing estimated calorie expenditure to calorie intake.

As indicated above, FIGS. 5A-5D are provided merely as an example. Other examples are possible and may differ from what was described with regard to FIGS. 5A-5D.

Figure 6:
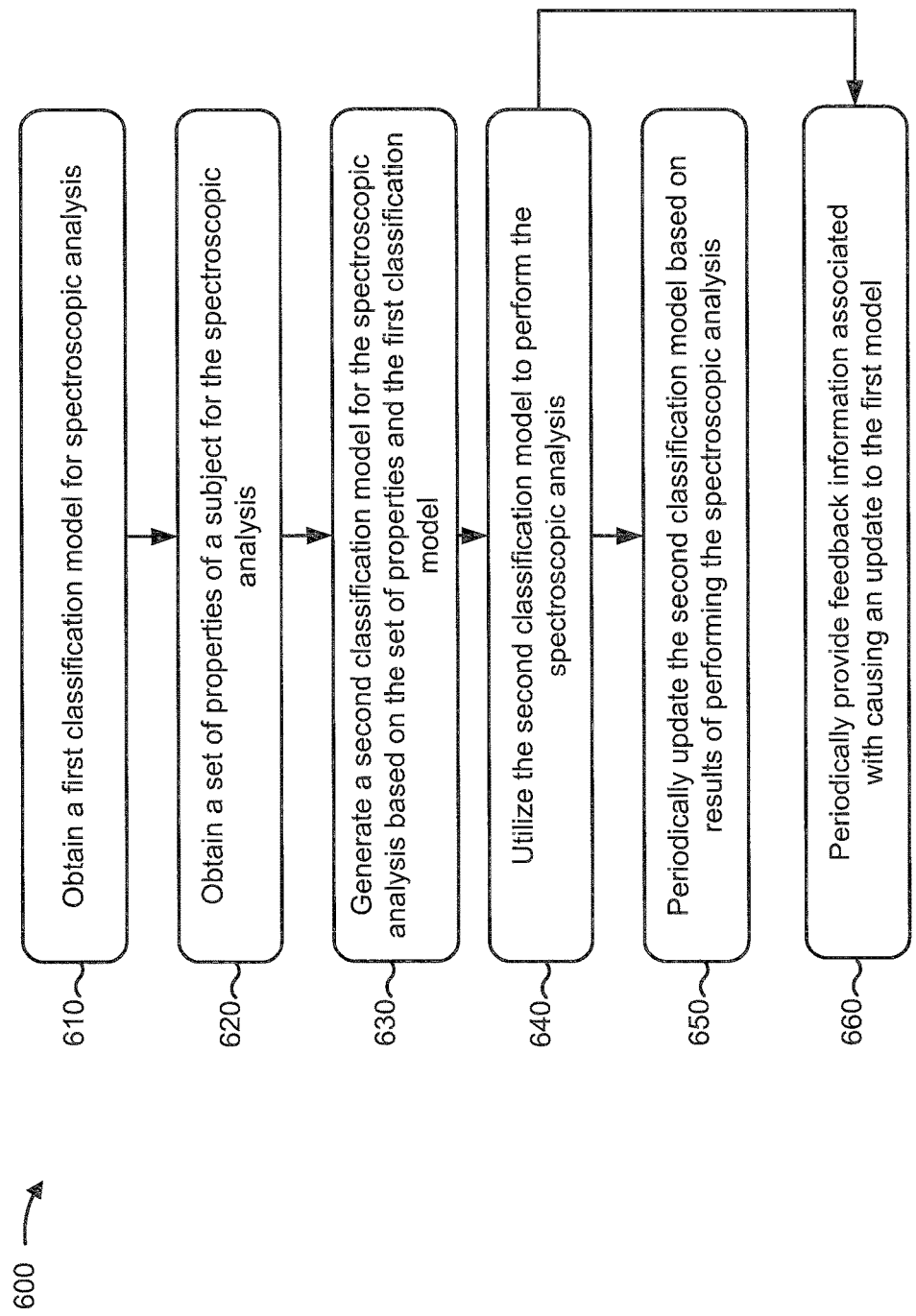
FIG. 6 is a flow chart of an example process for dynamically updating a classification model for spectroscopic analysis.

FIG. 6 is a flow chart of an example process 600 for dynamically updating a classification model for spectroscopic analysis. In some implementations, one or more process blocks of FIG. 6 may be performed by user device 210. In some implementations, one or more process blocks of FIG. 6 may be performed by another device or a group of devices separate from or including user device 210, such as application server 220.

As shown in FIG. 6, process 600 may include obtaining a first classification model for spectroscopic analysis (block 610). For example, user device 210 may obtain the first classification model for spectroscopic analysis. A classification model (e.g., a spectroscopic classification model) may refer to a model that may be utilized to identify a subject of spectroscopic analysis or a characteristic of the subject of spectroscopic analysis based on a chemometric signature obtained for the subject. For example, the classification model may include information associated with a set of chemometric signatures for a set of samples (e.g., a set of persons or a set of food items), and user device 210 may utilize the classification model to determine that a chemometric signature for a person corresponds to a particular characteristic (e.g., a blood glucose level) for the person. Similarly, user device 210 may utilize another classification model to determine that a chemometric signature for a food item corresponds to a particular nutritional content for the food item.

In some implementations, user device 210 may obtain the first classification model from a particular application server 220 associated with calibrating the first classification model. For example, the particular application server 220 may perform spectroscopic analysis on a calibration set (e.g., a set of identified subjects) using a spectrometer, and may utilize a processing technique (e.g., an optimization technique to distinguish between respective chemometric signatures for the calibration set) to generate the first classification model. In this case, user device 210 may receive the first classification model based on the calibration model being optimized by application server 220. In some implementations, user device 210 may obtain a particular classification model that is calibrated based on spectroscopic analysis performed on a set of persons. For example, application server 220 may perform a first spectroscopic analysis on a first person and a second spectroscopic analysis on a second person, and may generate the first classification model to account for differences in chemometric signatures (e.g., associated with blood glucose levels) for the first person and the second person (e.g., relating to differing body composition).

In some implementations, user device 210 may obtain the first classification model based on requesting the first classification model. For example, user device 210 may transmit a request for the first classification model, and may receive the first classification model from application server 220 based on transmitting the request. Additionally, or alternatively, user device 210 may obtain the first classification model from a data structure of user device 210. For example, user device 210 may include the first classification model stored via a data structure. In some implementations, user device 210 may generate the first classification model. For example, user device 210 may receive a set of chemometric signatures associated with a set of subjects, and may generate the first classification model based on the set of chemometric signatures. Additionally, or alternatively, user device 210 may perform a set of spectroscopic measurements on a set of known subjects to obtain chemometric signatures for the set of known subjects, and may generate the first classification model based on the chemometric signatures for the set of known subjects.

As further shown in FIG. 6, process 600 may include obtaining a set of properties of a subject for the spectroscopic analysis (block 620). For example, user device 210 may obtain the set of properties of the subject for spectroscopic analysis. In some implementations, user device 210 may determine the set of properties based on sensor data from one or more sensors. For example, user device 210 may utilize a sensor of user device 210 to determine a blood glucose level, a body temperature, or the like regarding a user based on sensor data recorded by the sensor. Additionally, or alternatively, user device 210 may communicate (e.g., via network 230) with a sensor (e.g., a Bluetooth enabled sensor), to receive sensor data associated with a property of the subject for the spectroscopic analysis (e.g., the user).

In some implementations, user device 210 may obtain one or more properties of the subject associated with categorizing the subject. For example, user device 210 may obtain information identifying a gender of the subject, an age of the subject, an ethnicity of the subject, or the like. In this case, user device 210 may obtain the information from a data structure stored by user device 210. Additionally, or alternatively, user device 210 may obtain the information from application server 220 (e.g., an application server associated with a health care provider and storing information regarding the user). In some implementations, user device 210 may obtain the information via a user interface. For example, user device 210 may generate a user interface and provide a set of prompts for display via the user interface, and may detect user interactions with the user interface associated with providing a set of responses to the set of prompts.

In some implementations, user device 210 may obtain a property of the subject of the spectroscopic analysis relating to a raw absorbance spectra of the subject of the spectroscopic analysis. For example, user device 210 may utilize an integrated spectroscopic sensor to perform a spectroscopic measurement of a user and determine a chemometric signature (e.g., a raw absorbance spectra) of the user. Additionally, or alternatively, user device 210 may communicate with a spectroscopic sensor to cause the spectroscopic sensor to determine a chemometric signature associated with the user, and user device 210 may receive the chemometric signature from the spectroscopic sensor based on communicating with the spectroscopic sensor.

As further shown in FIG. 6, process 600 may include generating a second classification model for the spectroscopic analysis based on the set of properties and the first classification model (block 630). For example, user device 210 may generate the second classification model for the spectroscopic analysis based on the set of properties and the first classification model. In some implementations, user device 210 may utilize a model optimization technique, such as a support vector machine classifier (SVM) optimization technique, or support vector regression (SVR) optimization technique, or the like, to optimize the first classification (or quantitative) model and generate the second classification (or quantitative) model. For example, user device 210 may optimize the first classification model (e.g., generated based on a set of persons) to generate the second classification model for performing classification relating to a user of user device 210 (e.g., determining a blood glucose level for the user). In this way, user device 210 accounts for differences between persons (e.g., body composition differences).

Additionally, or alternatively, user device 210 may optimize the first classification model (e.g., generated based on a first spectrometer associated with application server 220) to generate a second classification model for utilization with a second spectrometer associated with user device 210. For example, user device 210 may generate the second classification model for classifying food items based on spectroscopic sensor data obtained via the second spectrometer. In this way, user device 210 accounts for differences between spectrometers, thereby improving accuracy of spectrometry relative to utilizing a single classification model generated by application server 220 for each user device 210 utilized by each user.

As further shown in FIG. 6, process 600 may include utilizing the second classification model to perform the spectroscopic analysis (block 640). For example, user device 210 may utilize the second classification model to perform spectroscopic analysis. In some implementations, user device 210 may utilize the second classification model to determine a metric associated with a user (e.g., a subject of the spectroscopic analysis). For example, user device 210 may identify a characteristic (e.g., a blood glucose level, a triglycerides level, a ketone level, an insulin level, a skin condition, or a person's identity) based on spectroscopic sensor data associated with the user and the second classification model (e.g., a first chemometric signature, when classified based on the second classification model may correspond to a first triglycerides level for the user and a second chemometric signature, when classified based on the second classification model may correspond to a second triglycerides level. In this case, user device 210 may identify a health condition, such as a change to a skin thickness, a change to a skin density, a change to a skin collagen level, a change to a capillary density, or the like, based on detecting the characteristic.

In some implementations, user device 210 may utilize other sensor data regarding the user to perform the spectroscopic analysis. For example, user device 210 may determine, based on both a chemometric signature of a user and skin conductivity sensor data regarding the user, that the user is associated with a particular skin condition. Similarly, user device 210 may determine, based on both a chemometric signature of a food item and a volumetric analysis of the food item, a nutritional content of the item (e.g., a calorie content, a carbohydrate content, a protein content, or a fat content). In this way, user device 210 may combine sensor data from multiple sensors to determine and provide health information associated with a user.

In some implementations, user device 210 may provide information identifying a health condition based on performing the spectroscopic analysis. For example, user device 210 may generate a user interface, and may provide information identifying the health condition for display via the user interface. Additionally, or alternatively, user device 210 may provide information identifying the health condition to application server 220 (e.g., for inclusion in a patient medical record associated with the user). Additionally, or alternatively, user device 210 may provide information identifying a nutritional content of a food item. In some implementations, user device 210 may provide the results of performing the spectroscopic analysis for further processing. For example, user device 210 may perform the spectroscopic analysis, and may include data identifying the spectroscopic analysis in a dataset that is processed to determine and provide health information as described herein with regard to FIG. 4.

As further shown in FIG. 6, process 600 may include periodically updating the second classification model (block 650). For example, user device 210 may periodically update the second classification model. In some implementations, user device 210 may optimize the second model. For example, when user device 210 performs a spectroscopic analysis of a user, user device 210 may utilize the spectroscopic analysis and/or other sensor data to refine the second model using an optimization technique, such as an SVM optimization technique or the like. In this case, user device 210 may utilize the refined second model for performing a subsequent spectroscopic analysis. In this way, user device 210 improves accuracy of the second classification model relative to utilizing the second classification model without performing a refinement procedure based on spectroscopic analysis and/or other sensor data. Furthermore, over time, the model continues to become more accurate and/or more specific to the user of the model, thereby permitting user device 210 to perform more accurate identifications of characteristics of the user, diagnoses of conditions of the user, or the like. Moreover, based on utilizing the SVM optimization technique, user device 210 reduces a utilization of processor and/or memory resources as well as reducing time intensively relative to generating a new classification model. Furthermore, an incremental training approach may permit user device 210 to develop an accurate model as sensor data is received by user device 210 rather than requiring sufficient processing and/or memory resources to generate an initial model based on large quantities of sensor data related to increasing quantities of sensors related to the Internet of Things.

As further shown in FIG. 6, process 600 may include periodically providing feedback information associated with causing an update to the first classification model (block 660). For example, user device 210 may provide feedback information associated with causing an update to the first classification model. In some implementations, user device 210 may provide information identifying the second classification model to cause an update to the first classification model. For example, user device 210 may provide information identifying the second classification model to application server 220 to cause application server 220 to update the first classification model.

In some implementations, user device 210 may provide information identifying sensor data obtained by user device 210 to cause the update to the first classification model. For example, when user device 210 obtains sensor data indicating a particular body temperature and performs a spectroscopic measurement of a user with the particular body temperature to obtain a chemometric signature for the user at the particular body temperature, user device 210 may provide information identifying the particular body temperature and the chemometric signature for inclusion in the first classification model (e.g., for utilization in identifying the particular body temperature based on a similar chemometric signature).

Additionally, or alternatively, user device 210 may provide demographic information to update the first classification model. For example, when the first classification model is generated based on chemometric signatures corresponding to blood glucose levels of a group of men, user device 210 may determine a chemometric signature corresponding to a blood glucose level for a woman. In this case, user device 210 may transmit information identifying the chemometric signature for the women to cause the first classification model to be optimized, thereby performing distributed calibration of the model to improve accuracy of the model relative to utilizing a statically calibrated classification model generated based on a limited group of samples (e.g., the group of men).

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7A:
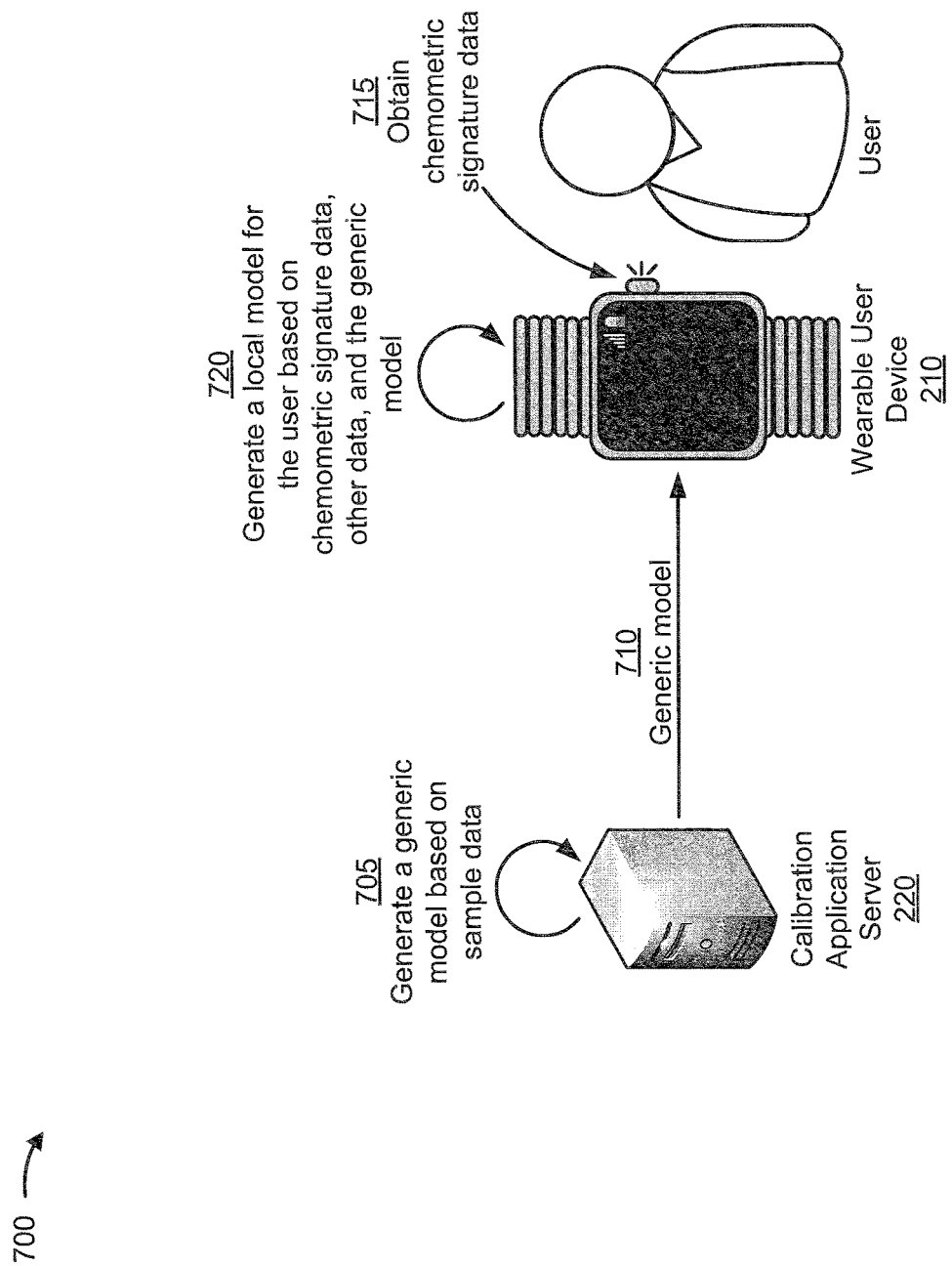
FIGS. 7A and 7B are diagrams of an example implementation relating to the example process shown in FIG. 6.
Figure 7B:
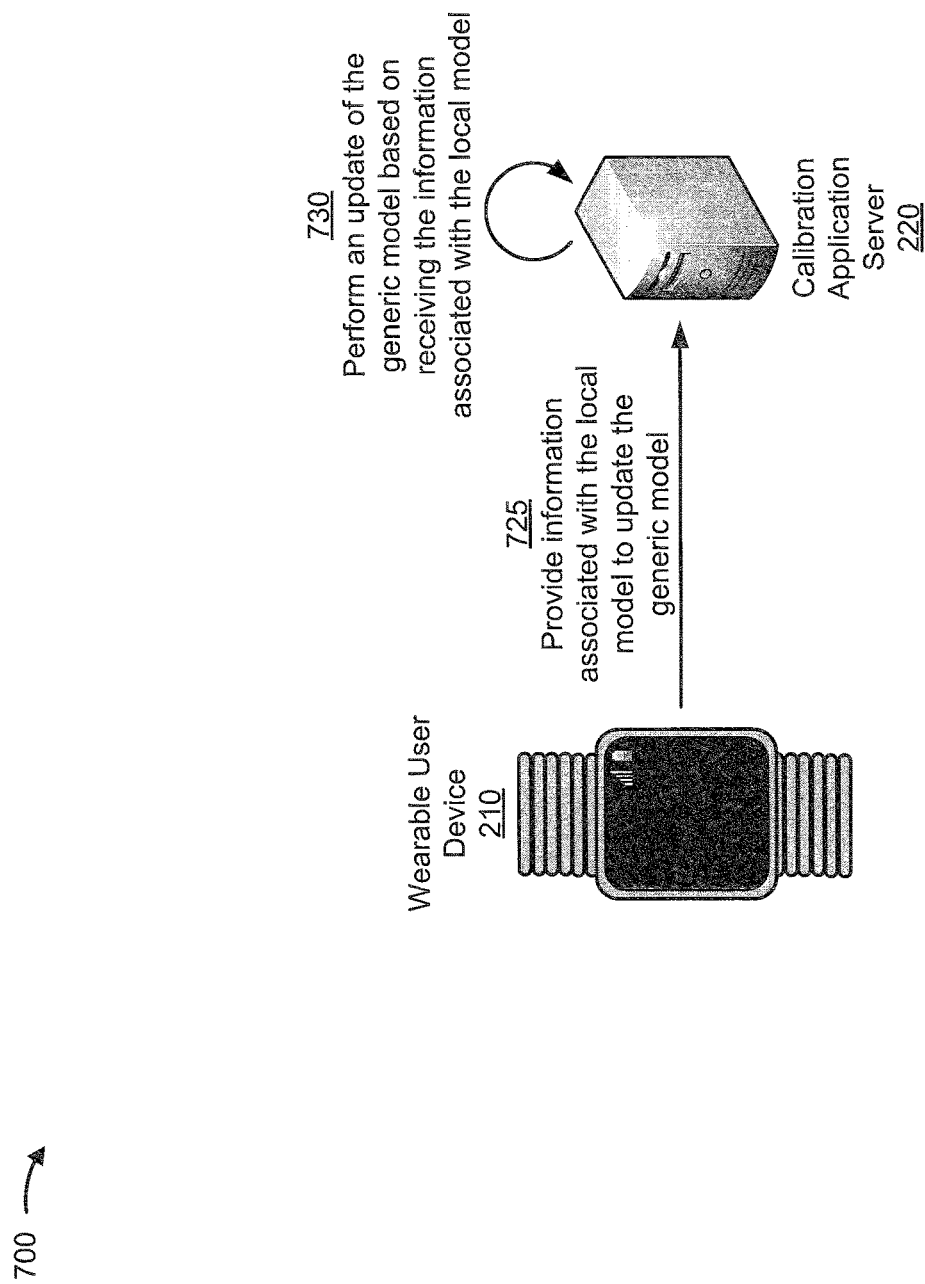

FIGS. 7A and 7B are diagrams of an example implementation 700 relating to example process 600 shown in FIG. 6. FIGS. 7A and 7B show an example of dynamically updating a classification model for spectroscopic analysis.

As shown in FIG. 7A, and by reference number 705, calibration application server 220 may generate a generic model (e.g., a generic classification model) based on sample data, obtained via a spectroscopic sensor associated with calibration application server 220, relating to a set of sample persons. As shown by reference number 710, wearable user device 210 receives the generic model from calibration application server 220. As shown by reference number 715, wearable user device 210 may obtain chemometric signature data relating to a user, such as a chemometric signature of a portion of the user's body. As shown by reference number 720, wearable user device 210 may utilize an SVM optimization technique to generate a local model (e.g., another classification model) for the user based on the chemometric signature data, other data, such as sensor data (e.g., a heart rate of the user, a skin conductivity of the user, or a blood glucose level of the user), demographic data (e.g., an age of the user, a body mass index of the user, or a gender of the user), or the like. Assume that wearable user device 210 stores the local classification model for utilization in classifying one or more other chemometric signatures obtained regarding the user (e.g., for diagnosing a condition of the user).

As shown in FIG. 7B, and by reference number 725, wearable user device 210 provides information associated with the local model to update the generic model, such as the chemometric signature data, the one or more other chemometric signatures, the data regarding the user, or the like. As shown by reference number 730, calibration application server 220 is caused to perform an update of the generic model based on receiving the information associated with the local model.

As indicated above, FIGS. 7A and 7B are provided merely as an example. Other examples are possible and may differ from what was described with regard to FIGS. 7A and 7B.

In this way, user device 210 utilizes sensor data from multiple sensors to provide health information regarding a user, improve calibration of one or more sensors (e.g., calibration of a classification model associated with a spectroscopic sensor), or the like. Moreover, based on utilizing sensor data form multiple sensors, user device 210 reduces a cost and power consumption associated with requiring a device for each sensor. Furthermore, based on utilizing an optimization technique to calibrate the spectroscopic sensor, user device 210 reduces a utilization of processing and/or memory resources relative to generating a new classification model each time additional sample data and reduces cost relative to generating a classification model based on sufficient sample data to perform all classifications without refinement.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method, comprising:
    determining, by a device, an activity level of a user based on first sensor data relating to the activity level of the user from a set of sensors of the device;
    determining, by the device, second sensor data based on spectroscopic sensor data from a spectroscopic sensor of the device;
    generating, by the device, a local model for the user based on a generic model generated by one or more other devices and based on the second sensor data;
    determining, by the device, information regarding a user compliance with a stored diet and exercise plan for the user based on the local model for the user, the activity level of the user, and a nutritional content of a set of food items,
        the stored diet and exercise plan including a goal relating to the activity level of the user; and
    providing, by the device, a recommendation relating to the user compliance with the stored diet and exercise plan based on the information regarding the user compliance with the stored diet and exercise plan.

2. The method of claim 1, further comprising:
obtaining a plurality of images from an imaging sensor; and
determining the nutritional content of the set of food items based on the plurality of images.

3. The method of claim 1, further comprising:
determining a volume of the set of food items based on a plurality of images; and
determining the nutritional content of the set of food items based on the volume.

4. The method of claim 1, where the second sensor data includes a chemometric signature.

5. The method of claim 1, further comprising:
receiving the generic model from a calibration application server,
where the one or more other devices include the calibration application server,
where the generic model comprises a generic classification or quantitative model for spectroscopic analysis, and
where the local model for the user comprises a local classification or quantitative model for spectroscopic analysis based on the generic classification or quantitative model and third sensor data.

6. The method of claim 5, where generating the local model for the user includes utilizing an optimization technique.

7. The method of claim 1, further comprising:
determining a calorie expenditure by the user based on the first sensor data; and
where determining the user compliance with the stored diet and exercise plan comprises:
determining that a calorie intake by the user associated with consumption of the set of food items exceeds the calorie expenditure by a threshold amount,
the calorie intake being related to the nutritional content of the set of food items.

8. The method of claim 7, further comprising:
determining an amount of exercise that corresponds to the threshold amount,
where providing the recommendation comprises:
providing information identifying the amount of exercise that corresponds to the threshold amount.

9. A system, comprising:
one or more sensors;
a spectrometer;
one or more memories; and
one or more processors, coupled to the one or more memories, configured to cause the system to:
receive, from a server, a generic model generated by the server;
determine data based on spectroscopic data from the spectrometer;
generate a local model for a user of the system based on the generic model and based on the data;
determine, based on the local model for the user and one or more chemometric signatures obtained regarding the user, a condition of the user; and
provide information based on the condition of the user and a compliance of the user with a plan.

10. The system of claim 9, wherein the one or more processors are further configured to:
obtain a plurality of images from an imaging sensor; and
determine the compliance of the user based on the plurality of images.

11. The system of claim 9, wherein the one or more processors are further configured to:
determine a volume of a set of food items based on a plurality of images; and
determine the compliance of the user based on the volume.

12. The system of claim 9, where the data includes a chemometric signature of the one or more chemometric signatures.

13. The system of claim 9, wherein the generic model is a generic classification model for spectroscopic analysis.

14. The system of claim 9, where the one or more processors, to generate the local model for the user, are configured to utilize a support vector machine classifier (SVM) optimization technique.

15. The system of claim 9, wherein the one or more processors are further configured to:
determine, based on sensor data, a calorie expenditure by the user; and
determine the compliance of the user based on a calorie intake by the user exceeding the calorie expenditure by a threshold amount.

16. The system of claim 9, wherein the information identifies an amount of exercise.

17. A non-transitory computer-readable medium storing a set of instructions, the set of instructions comprising:
one or more instructions that, when executed by one or more processors of a device, cause the device to:
determine an activity level of a user, of the device, based on first sensor data from one or more sensors of the device;
determine second sensor data based on spectroscopic data from a spectrometer of the device;
generate a local model for the user based on a generic model generated by one or more other devices and based on the second sensor data;
determine, based on the local model, a condition of the user;
determine a user compliance, associated with the condition, based on the activity level of the user; and
provide information based on the user compliance.

18. The non-transitory computer-readable medium of claim 17, wherein the one or more instructions further cause the device to:
obtain a plurality of images from an imaging sensor; and
determine nutritional content of a set of food items based on the plurality of images,
wherein the user compliance is further based on the nutritional content of the set of food items.

19. The non-transitory computer-readable medium of claim 17, wherein the one or more instructions further cause the device to:
determine a volume of a set of food items based on a plurality of images,
wherein the user compliance is further based on the volume.

20. The non-transitory computer-readable medium of claim 17, where the second sensor data includes a chemometric signature.

* * * * *